(12) United States Patent
Peters

(10) Patent No.: US 8,231,584 B2
(45) Date of Patent: Jul. 31, 2012

(54) CONTRAST FLUID DELIVERY SYSTEM

(76) Inventor: Jean-Pierre Peters, Hasselt (BE)

(*) Notice: Subject to any disclaimer, the term of this patent is extended or adjusted under 35 U.S.C. 154(b) by 251 days.

(21) Appl. No.: 11/944,800

(22) Filed: Nov. 26, 2007

(65) Prior Publication Data

US 2008/0086094 A1  Apr. 10, 2008

Related U.S. Application Data

(63) Continuation-in-part of application No. PCT/EP2006/062554, filed on May 23, 2006.

(30) Foreign Application Priority Data

May 26, 2005 (EP) ..................... 05447122

(51) Int. Cl.
 *A61M 5/00* (2006.01)
 *A61M 25/00* (2006.01)
(52) U.S. Cl. ........ 604/257; 604/246; 604/247; 604/264; 604/905
(58) Field of Classification Search ............ 604/246, 604/247, 30, 523, 533, 534, 535, 537, 538, 604/93.01, 905, 256, 257, 258, 264, 272, 604/500, 506, 507, 539, 80
See application file for complete search history.

(56) References Cited

U.S. PATENT DOCUMENTS

| 4,258,712 A * | 3/1981 | Harms et al. ............ 604/81 |
|---|---|---|
| 4,755,172 A * | 7/1988 | Baldwin ............ 604/131 |
| 4,772,265 A * | 9/1988 | Walter ............ 604/164.08 |
| 4,820,288 A * | 4/1989 | Isono ............ 604/534 |
| 4,950,254 A * | 8/1990 | Andersen et al. ............ 604/247 |
| 4,998,926 A * | 3/1991 | Alchas ............ 604/251 |
| 5,226,886 A * | 7/1993 | Skakoon et al. ............ 604/153 |
| 5,334,170 A * | 8/1994 | Moroski ............ 604/80 |
| 5,593,385 A * | 1/1997 | Harrison et al. ............ 604/83 |
| 5,685,842 A * | 11/1997 | Drivas ............ 604/500 |
| 6,800,072 B2 * | 10/2004 | Patzer ............ 604/260 |
| 7,331,938 B2 * | 2/2008 | Nemoto ............ 604/131 |
| 2003/0070273 A1 * | 4/2003 | Kust ............ 29/426.1 |
| 2003/0171721 A1 * | 9/2003 | Enomoto et al. ............ 604/247 |
| 2004/0002685 A1 * | 1/2004 | Patzer ............ 604/257 |
| 2004/0102738 A1 * | 5/2004 | Dikeman et al. ............ 604/256 |

FOREIGN PATENT DOCUMENTS

DE 203 01 094 U1 4/2003
WO WO 03/086528 A1 10/2003

* cited by examiner

*Primary Examiner* — Kevin C Sirmons
*Assistant Examiner* — Shefali Patel
(74) *Attorney, Agent, or Firm* — Sughrue Mion, PLLC

(57) ABSTRACT

A disposable set (5) for establishing a fluid connection between a fluid dispensing unit (17) and a dosing device adapted to dispense a fluid into a patient's vein. The disposable set comprises a length of tubing (15) having a first (1) and a second (10) tubing part. The first tubing part (1) having a one-way valve (3) which permits a fluid flow from the dispensing unit (17) towards the dosing device and to prevent a backward fluid flow from the dosing device towards the dispensing unit. The first and second tubing part are in fluid connection with each other by means of a releasable connection device (11, 12), which is adapted to permit a back flow from a patient in a released position of the releasable connection device and to prevent a back flow from the patient in a closed position.

11 Claims, 2 Drawing Sheets

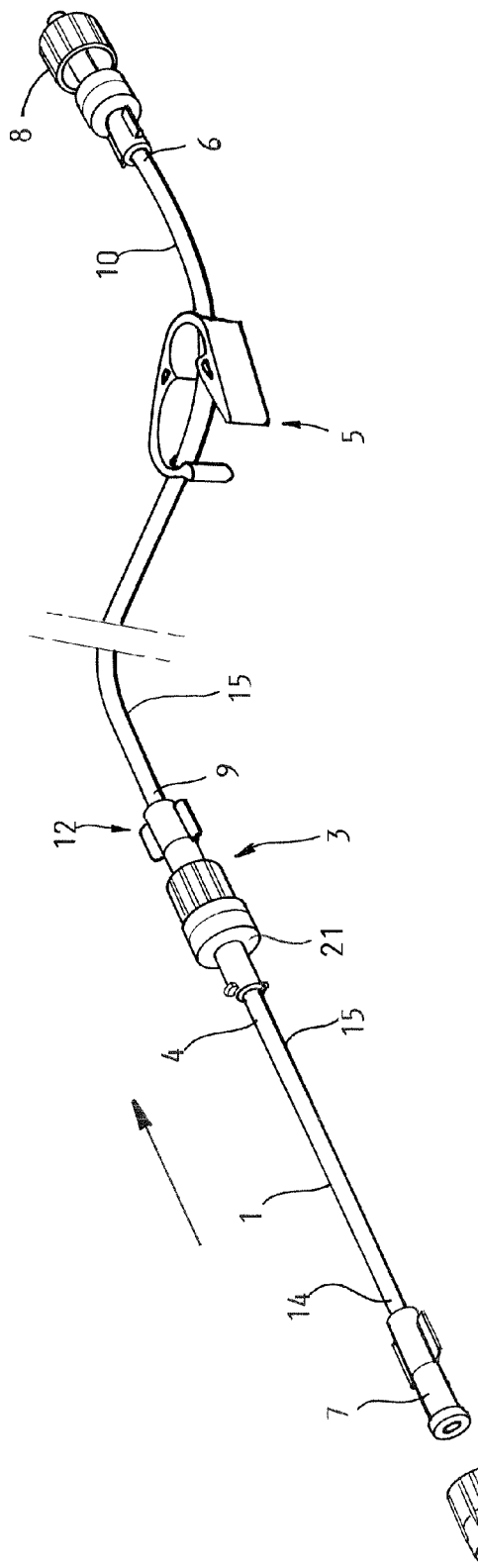
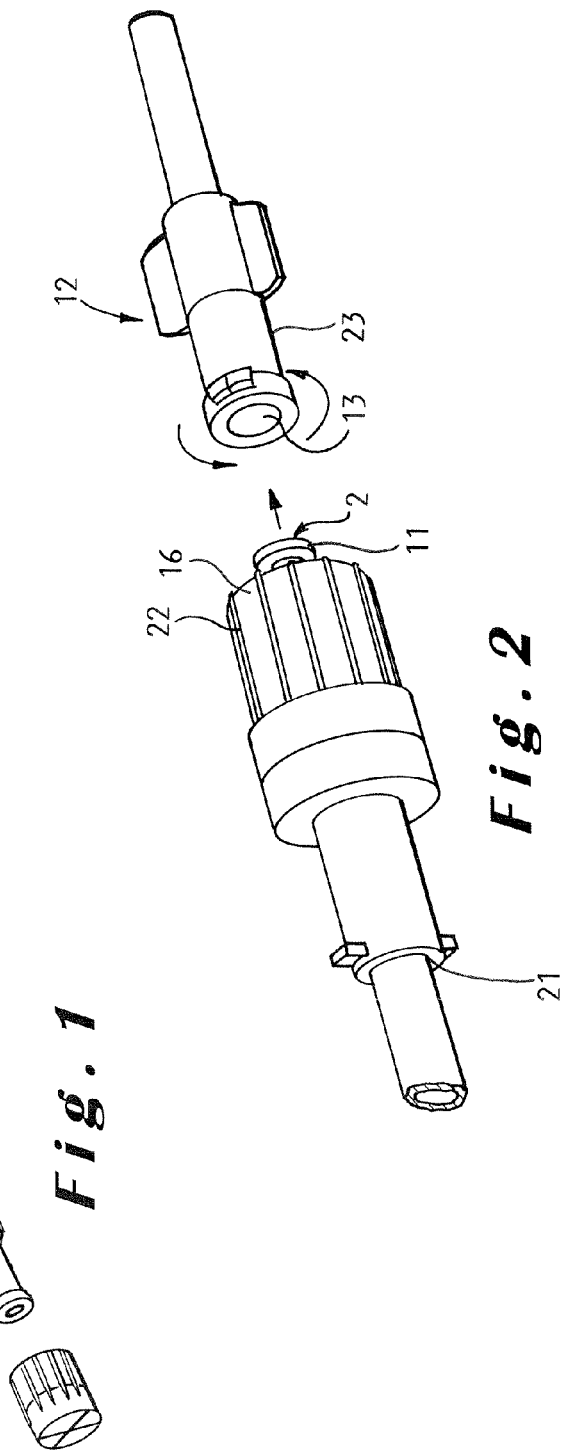

CONTRAST FLUID DELIVERY SYSTEM

CROSS-REFERENCE TO RELATED APPLICATIONS

This application is a Continuation-in-Part of International Application No. PCT/EP06/062554, filed May 23, 2006, which is incorporated herein by reference, which claims priority to European Patent Application No. 05447122.2, filed May 26, 2005.

BACKGROUND OF THE INVENTION

1. Field of the Invention

The present invention relates to a disposable set for establishing a fluid connection between a fluid dispensing unit and a dosing device adapted to dispense the fluid into a patients' vein, wherein the disposable set essentially consists of a length of a tubing for establishing a fluid connection from the dispensing unit towards and into the dosing device, according to the preamble of the first claim.

2. Description of the Related Art

Contrast medium dispensing systems are well known in the art. The known dispensing systems usually comprise a spike at one end for engaging the reservoir containing the contrast medium, and on the other end a mechanism with a luer connector for coupling the container to one port of a manifold. Another port of the manifold is coupled to a syringe adapted to administer the fluid into the patient's vein. To reduce waste, many contrast medium dispensing systems include a reservoir between the spike and the luer connector to temporarily hold a quantity of contrast medium. In an effort to avoid cross contamination between patients, many systems include a reusable set carrying the spike and a disposable set carrying the outlet luer connector providing the connection to the syringe, a pair of mating luer connectors for selectively joining the reusable and disposable set and a check valve downstream the spike. By switching the disposable set, one large container of contrast medium may be used with multiple patients.

An example of a contrast fluid dispensing system is disclosed in U.S. Pat. No. 6,800,072. The dispensing system disclosed in U.S. Pat. No. 6,800,072 comprises a tube with a first end connected to a spike adapted to be coupled in fluid communication to a bulk source of contrast media. A second end of the tube comprises a first part of a luer connector which is provided to co-operate with a corresponding second part of the luer connector mounted to a disposable set. The disposable set comprises a reservoir which is in fluid connection with a further tubing which is adapted to conduct the contrast medium from the reservoir to a port of a manifold through a one-way valve. A syringe for delivering the contrast medium into the patients' vein is connected to an administering tubing which is connected to another port of the manifold. The reservoir comprises a cap member which is adapted to reduce the risk to splattering and the ensuing formation of bubbles in the reservoir.

The dispensing device disclosed in U.S. Pat. No. 6,800,072 however presents the disadvantage that it does not permit to check in the vicinity of the syringe whether or not the syringe been well inserted into the patients' vein, and does not permit to establish whether or not the contrast medium is actually flowing into the patients' vein and not into the surrounding tissue. Besides this the dispensing device of U.S. Pat. No. 6,800,072 does not contain any means which inhibit back flow of blood from the patients' vein towards the reservoir containing the contrast medium and further towards the bulk source. Such a back flow is to be avoided as it is a basis of contamination of the system, where a next patient may be contaminated with foreign material, possibly from a former patient.

WO03/086528 discloses a one-way valve for use with tubes for medical use in particular peritoneal dialysis, which combines the functions of mechanically connecting the end parts of an infusion/drainage line and an access line connected to the peritoneum of a patient, and of regulating the flow to provide a flow with few or no areas of stagnation. Thereto the one-way valve comprises a main body with at least one fluid passage, which is attachable to the end of a first tube and which comprises an elastically deformable shut-off element to provide or prevent fluid communication between the end parts of the fluid passage. The elastically deformable shut-off element has a longitudinal axis of symmetry and is designed to deform symmetrically during the transition from a first condition where fluid communication is prevented, and a second condition where fluid communication is permitted. However, as the one-way valve of WO03/086528 is provided for use in peritoneal dialysis, verification of correct insertion of the access line into the peritoneum is not a problem which is addressed.

U.S. Pat. No. 5,593,385 discloses a dispensing system for introducing contrast media intravascularly during catherization procedures. The system comprises a first tubing segment which on one end is provided with a spike connecting the first tubing segment to a bottle containing the contrast medium. The first tubing segment is connected to the second tubing segment by means of a stopcock and a luer connector. A top check valve is mounted at the end part coupling the second tubing segment to the first tubing segment to prevent reflux from the second tubing part. The second tubing part is connected to a third tubing part by means of a bottom check valve and stop cock, the bottom check valve preventing reflux from the third tubing segment to the second tubing segment. The third tubing segment is coupled to a conventional manifold and further towards the vascular system. Air may be admitted through the stopcock to enhance the flow of the contrast medium. Due to the presence of the luer connector, the second and third tubing may be dispensed after use, and the first tubing segment may be re-used. U.S. Pat. No. 5,593,385 does not disclose means which permit to check whether a syringe mounted to a tubing connecting the manifold to the patient, has been correctly inserted into the patients' vein.

In view of preventing contamination of the manifold or reservoir and the fixed part of a fluid dispensing system, there is thus a need to a dispensing device containing a tool which permits to verify whether or not a dosing device, in particular an injection needle, has been well inserted into a patients' vein in such a way that the fluid flows from the fluid dispensing system into the vein thereby minimizing the risk to dispensing of the fluid into surrounding tissue.

BRIEF SUMMARY OF THE INVENTION

It is therefore an object of the present invention to provide a device which permits connecting a manifold or fluid reservoir which forms part of the fixed part of a fluid dispensing system to the dosing device which is adapted for insertion into a patients' vein, in such a way that verification whether or not the dosing device has been correctly inserted into the patients' vein may be established.

It is a further object of this invention to provide a device with which there is a minimal risk that fluid from a dispensing system is administered unwontedly into surrounding tissue. p It is a further object of this invention to provide a device which permits minimizing the risk to contamination of the fixed part of the fluid dispensing system, even to prevent such contamination.

This problem is solved with the disposable set showing the technical features of the characterizing part of the first claim.

Thereto, the disposable set of this invention is characterized in that the tubing consists essentially of a first (1) and a second (10) tubing part, wherein the first tubing part (1) comprises a first end connector (2, 11, 16, 22) to establish at a first end part (4) a connection to a third end connector (12, 13) at a second end part (9) of the second tubing part (10), and a second end connector (7) at a second end part (14) to establish a connection towards the fluid dispensing unit, wherein the second tubing part (10) comprises a fourth end connector (8) which is provided to establish at a first end part (6) of the second tubing part a connection towards the dosing device and the patient and a third end connector (12, 13) at a second end part (9) of the second tubing part (10) to establish a connection to the first tubing part (1), wherein the first tubing part (1) comprises a one-way valve (3) which is provided to permit a fluid flow from the dispensing unit (17, 18) towards the dosing device and to prevent a backward fluid flow from the dosing device towards the dispensing unit, wherein the first end part (4) of the first tubing part and the second end part (9) of the second tubing part (10) are in fluid connection with each other in a liquid tight manner by means of a releasable connection device (11, 12), which releasable connection in the released position of the releasable connection is adapted to permit a back flow from the patient into the second tubing part (10) and to prevent a back flow from the patient in the direction of the releasable connection device (11, 12) in the closed position of the releasable connection.

When in use, the second end part of the first tubing part of the disposable set of this invention may be coupled to the manifold, which is in turn connected to a fluid reservoir containing the contrast medium to be administered to the patient. The disposable set may however be coupled to any other fixed part of a fluid dispensing system. The opposite first end of the first tubing part is coupled to the second end part of the second tubing part. The first end of the second tubing is coupled to an injection needle or any other dosing device which is to be inserted in the patients' vein. A complete filling of both the tubing and the needle with fluid at the time the injection needle is inserted in the patients' vein must be ensured as delivering of air into the vein would expose the patient to high risk. As soon as the dosing device—i.e. the injection needle has been inserted into the patients' vein and the connection with the reservoir has been established at the second end part of the first tubing, with the releasable connection between the first and second tubing part in the connected state, a fluid flow from the reservoir into the injection needle and the patients' vein is permitted.

By disconnecting the releasable connection device, the first tubing part is disconnected from the second tubing part, the second tubing part is open to the air at the position of its first end part and permits aspiration of the injection needle. Thus a back flow of blood from the patients' vein into the second tubing part is permitted and the so-called reflux blood control of blood from the vein into the dosing device and part of the tubing may be carried out. Blood reflux is an indication that the dosing device or injection needle has been correctly inserted in the patients' vein. Once a reflux has been observed, the releasable connection device is brought into the connected state and blood reflux towards the manifold is inhibited by the presence of the one-way valve and pressure from the first tubing part. The control that the dosing device or injection needle has been well inserted in the patients' vein is important as the risk to flowing of fluid from the reservoir into tissue surrounding the vein needs to be minimized as this may involve necrosis of surrounding tissue.

In other words, with the disposable set of this invention the second tubing part may be temporarily disconnected from the first tubing part to verify whether the dosing device has been correctly inserted into the patients' vein. Although the reflux control involves a back flow of blood from the patient into the tubing, the risk to contaminating the manifold is nihil as the one-way valve present in the first tubing part is positioned between the releasable connection and the manifold and inhibits blood flow through the one way valve and towards the fixed part. Besides that, the risk to contamination is further reduced by ensuring that the part of the first tubing which extends between the one way valve and the connection to the fixed part of the fluid dispensing system is sufficiently long.

According to a preferred embodiment of the invention, the tubing consists essentially of a first and a second tubing part, wherein the first tubing part (1) consists of a tubing with
 a first end connector which permits establishing a connection to a third end connector at the second end part of the second tubing part
 a second end connector at a second end part of the tubing to establish a connection towards the fluid dispensing unit,
 a one-way valve mounted to the tubing which is provided to permit a fluid flow from the dispensing unit towards the dosing device and to prevent a backward fluid flow from the dosing device towards the dispensing unit,
wherein the second tubing part consists of a tubing with
 a fourth end connector for establishing at a first end part of the second tubing part a connection towards the dosing device and the patient
 and a third end connector at a second end part of the second tubing part to establish a connection to the first tubing part
wherein the first end part of the first tubing part and the second end part of the second tubing part are in fluid connection with each other in a liquid tight manner by means of a releasable connection device, which releasable connection in the released position of the releasable connection is adapted to permit a back flow from the patient into the second tubing part and to prevent a back flow from the patient in the direction of the releasable connection device in the closed position of the releasable connection.

According to a preferred embodiment of the invention, the releasable connection device comprises a first and a second connector part, the second connector part is fastened to a second end part of the second tubing part and the first connector part is mounted to an outlet side of the one-way valve along which outlet side the fluid flows from the one way valve in the direction of the second tubing part. The risk to contamination towards the reservoir may be further reduced by having a second tubing part located at a position proximal to the patient with a relatively longer length as compared to the first tubing part.

Handling of, i.e. disconnecting and re-establishing the releasable connection is facilitated in case the first connector part is positioned on an end part of the one-way valve on the side pointing towards the second tubing part.

The present invention also relates to a fluid dispensing system containing the above described disposable set.

The present invention also relates to the use of the above-described disposable set and fluid dispensing system for dispensing a fluid into a vein of a patient.

The present invention further relates to the use of the above-described disposable set and fluid dispensing system for dispensing a fluid to a patient.

The present invention also relates to a method for verifying blood back flow from a patient towards a fluid dispensing reservoir using the above-described disposable set and fluid dispensing system, according to which a dosing device is inserted into a patients' vein, the dosing device is connected to a second tubing part, the releasable connection is opened to permit a back flow from the patients' vein into the second tubing part and the releasable connection is re-established after the back flow of blood into the second tubing part has occurred and has been observed.

The invention is further elucidated in the attached figure and description of the figure.

BRIEF DESCRIPTION OF THE DRAWINGS

FIG. 1 shows a possible embodiment of the disposable set of the present invention.

FIG. 2 shows a detail of the one-way valve integrated into the disposable set of the present invention.

DETAILED DESCRIPTION OF THE INVENTION

Figure 3:
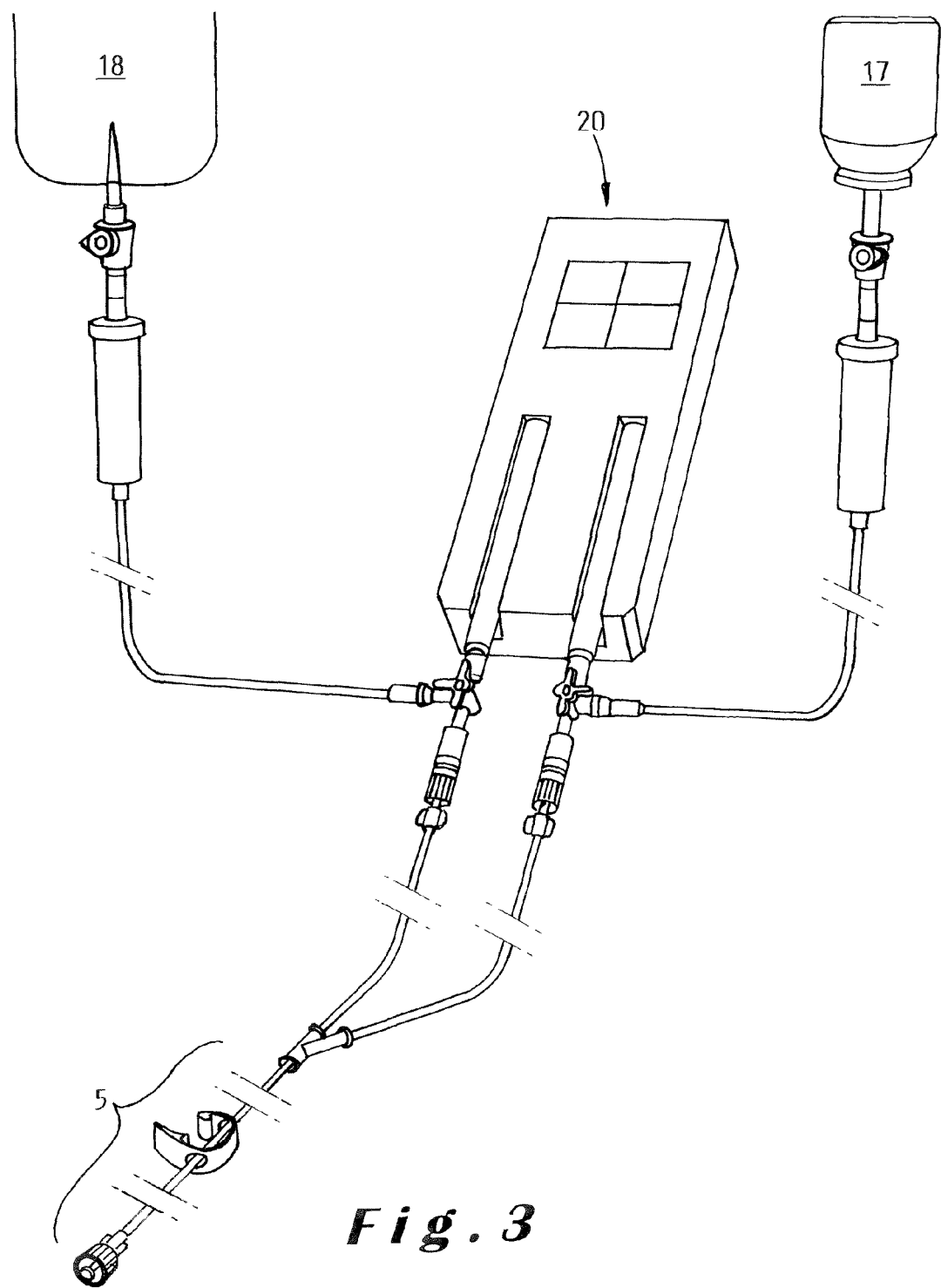
FIG. 3 shows the disposable set of the present invention build into a fluid dispensing system.

As can be seen from FIG. 1, the disposable set 5 of the present invention comprises a tubing 15 with a first 1 and a second tubing part 10. The first tubing part 1 is located distal from the patient, the second tubing part 10 is located proximal to the patient. The first and second tubing part 1, 10 are in fluid connection with each other by means of a releasable connection device 11, 12. The first tubing part 1 comprises a first and a second end part 4, 14; the second tubing part 10 comprises a first and a second end part 6, 9. The first end part 4 of the first tubing part 1 is connected to the second end part 9 of the second tubing part 10 by means of the releasable connection device. The releasable connection device comprising a first connector part 22 which is mounted to the first end part 4 of the first tubing part 1, and a second connector part 23 which is mounted to the second end part 9 of the second tubing part 10.

The first tubing part contains a one way valve 3, which is provided to permit a fluid flow from the fluid dispensing unit 17, 18 towards the patient, or in other words from the second end part 14 towards the first end part 4 of the first tubing part 1. The one way valve 3 is provided to prohibit a fluid flow from the patient towards the fluid dispensing unit 17, 18, or in other words from the second end part 9 of the second tubing part 10 to the second end part 14 of the first tubing part 1. The one way valve may be mounted somewhere centrally of the first tubing part 1, or shifted to one of the end parts. To facilitate manipulation, the one way valve is mounted in the proximity of the first end part 4 of the first tubing part 1, preferably at the end part.

Manipulation is further facilitated in that the first connector part 22 of the releasable connection 11 is mounted to an end part of the one-way valve 3. The connector can be made of any suitable connector known to the person skilled in the art, which permits to releasably connect two parts of a tubing, for example a luer connector or a bayonet coupling or any other coupling known to the person skilled in the art.

The second connector part 12 is mounted to a second end part 9 of the second tubing part 10. The first and second connector part 11, 12 are releasable connectible to each other in a liquid tight manner and permit a fluid flow from the fluid dispensing unit towards the patient as well as the reverse.

Usually the second tubing part 10 proximal to the patient will have a relatively longer length as compared to the first tubing part 1, to prevent that any contamination ends up in the fixed part 17, 18, 20 of the fluid dispensing system. Anyhow, although contamination originating from a patient may end up in the releasable connecting device 11, 12 the one way valve 3 will prevent further back flow towards the fluid dispensing unit 17, 18, forming the fixed part of the fluid dispensing system which is re-used with all patients. The risk to contamination of the fixed part may be further decreased by using a first tubing part 1 with a relatively long length. Within the scope of the present invention any one way valve considered suitable by the person skilled in the art may be used. Often the use of a one way valve made of a transparent material will be used as it assists in facilitating the control of the dispensing of the fluid.

A second end part 14 of the first tubing part 1 comprises a connector 7, for example a luer connector or any other suitable connector, for establishing a fluid connection towards the manifold or the fixed part of the fluid delivery device, that is re-used with every patient. In practice, the luer connector 7 will mostly be used to connect the dosing device to a manifold 20, which intervenes in dosing the contrast fluid contained in a reservoir 17 from that reservoir to the patient (see FIG. 3). The manifold 20 and reservoir 17 usually form part of the fixed part of the fluid delivery device.

A first end part 6 of the second tubing part 10 comprises a second connector, for example a luer connector 8 establishing the connection towards the dosing device with which the fluid is injected into the patients' vein. As a dosing device any suitable device known to a person skilled in the art may be used. A suitable example of a dosing device is a syringe or injection needle.

The disposable set 5 of the present invention may be in direct connection with the fixed, re-used part 17, 18, 20 of the fluid dosing device or it may be indirectly connected to it, for example in case other instruments are present between the disposable set and the fixed part 17, 18, 20 of the system. In that case, the first tubing part 1 serves as a kind of safety area, as it increases the distance between the patient and the manifold and/or the fluid reservoir 17, 20 and the fixed part of the device 17, 18, 20 that is re-used with every patient and in that way assists in preventing contamination of the fixed part of the device. Although this is not necessary, additional lengths of tubing may be provided between the first tubing part 1 and the fixed part of the fluid dispensing system, using any connecting means considered suitable by the person skilled in the art.

To minimize the risk to contaminating other devices or to introduce contamination from other sources, the device of this invention essentially consists of a first and a second tubing which are connected to each other by means of a releasable connection. The other end parts of the first and second tubings are adapted for connection respectively to the dosing device and to the patient. Preferably no provisions are present to permit connection of or to any additional devices. Or in other words the device of this invention consists of a tubing with an inlet for the fluid which is to be injected, an outlet for administering the fluid into the patient, whereby the tubing consists of a first and a second part which are releasably connectable to each other.

The releasable connection 11, 12, used in the disposable set of this invention may be any connection known to the person skilled in the art, as long as it contains a first and a second part which are releasable connectible to each other and wherein the second part 12 in the disconnected state is open to the air to permit aspiration and a back flow of blood from a patients' vein into the second tubing part 10.

The one way valve comprises in inlet side 21 along which fluid from the fluid dispensing unit 17, 18 enters the one way valve, and an outlet side 2 on the opposite side of the one way valve, along which the fluid leaves the one way valve towards the patient. To facilitate manipulation of the releasable connection, the first connector part 22 is mounted to the outlet side 2 of the one way valve 3. The first connector part 22 preferably comprises a luer lock flange which is adapted to be received in a corresponding duct 13 of the second connector part 23 in a liquid tight manner. With a first connector part mounted to the outlet side 2 of the one way valve, any back flow from the second tubing part 10 towards the first connector part 22 is withheld by the one way valve.

Preferably the first and second connector part 22, 23 are releasably connectible in a liquid tight manner by means of a threaded connection, provided on an outer wall of the duct 13 and an inner face of a circumferential wall 16 surrounding the flange over at least part of its length, as this provides a simple and quick opening and re-fastening. Thereby, the first flange 11 is adapted to be received in the corresponding second duct 13 in a liquid tight manner. However any other releasable connecting means may be used, provided the liquid-tight connection is respected.

The disposable system of the present invention is suitable for use with any fluid dispensing system for dispensing a fluid to a patient. The disposable system of this invention is particularly suitable for dispensing a fluid into veins, more particularly for dispensing contrast fluid into a patients' vein. However, the fluid dispensing system of this invention is suitable for dispensing any fluid to a patient and into a vein of a patient, for example the fluid dispensing system of this invention is suitable for use with pain pumps or dialysis devices. In that case reflux control may be required from another organ of the patient, and may not involve blood but another fluid originating from the patient. The fluid dispensing system of this invention may also be used in a situation where a patient is moved from one fluid dispensing unit to another, as there is no risk to contamination of the first tubing part which each time is connected to fluid dispensing unit 17, 18. In that case the injection needle or dosing device remains inserted into the patients' vein, the second end part 14 of the first tubing is each time disconnected from a previous fluid dispensing system and re-connected to the next system. This is a big advantage as an injection needle has to be inserted only once and the disposable set can be taken along with the patient in case a plurality of successive tests and treatments need to be carried out. This is time saving and permits to at least double the number of CT scans that can be done on one day.

The tubing may be made of any suitable material known to the person skilled in the art. However, when used to dispense contrast fluid, preferably polyvinylchloride. The dimensions of the first and second tubing part are not critical to the present invention and may be adapted by the person skilled in the art to the intended application. In CT scan systems the distance and thus the length of the tubing between the injection needle and the reservoir containing the contrast medium will often be approximately 1 meter. Such tubing may for example have an internal volume of approximately 5-10 ml, the over-all content of the contrast fluid reservoir being approximately 110 ml. However, with MRI imaging often the fluid is injected into the patients' vein under pressure and a somewhat larger distance needs to be bridged. To minimize the risk to local expansion of the tubing and to optimize the so-called bolus, usually use will be made of tubing having a relatively thicker material thickness. As in MR imaging the contrast fluid volume is often limited to 10-15 ml, usually use will be made of a tubing having a smaller internal diameter and an internal volume of only approximately 3 ml, although this may be somewhat more or somewhat less. A commonly used length of tubing in MR imaging is approximately 120 cm, although this may be longer or shorter depending on the nature of the device used. However, the fluid dispensing system of this invention is not limited for use with contrast medium only, but is suitable for use with a wide variety of fluids that are to be delivered to a patient.

When in use, the first and second tubing part 1, 10 are used in the connected state of the connecting device 11, 12. The second tubing part 10 is connected to an injecting needle through the second luer connector 8. The first tubing part 1 is connected to the fluid dispensing system 20 through the first luer connector 14. After the connection has been established, the system is usually flushed with a physiologic fluid contained in reservoir 18. After the flushing has been terminated, the connection of the manifold 20 towards the reservoir 18 is closed, and the connection of the manifold towards the contrast fluid reservoir 17 is opened, so that contrast fluid may flow into the tubing 15. After having completely filled tubing 15 and the injection needle, the needle is inserted into the patients' vein. Reflux control, to verify whether the injection needle has been inserted in a correct manner into the patients' vein is done by disconnecting the first and second connector part 11, 12, aspirating the second tubing part 10 containing the injection needle and verifying whether or not there is a back flow of blood from the patient into second tubing part 10. After back flow into the second tubing part 10 has been observed, connection of the first and second connector part 11, 12 is re-established, blood back-flow into the second tubing part does no longer occur and flow of contrast fluid from reservoir 17 into the patients' vein may be permitted. Fluid is permitted to flow as indicated by the arrows in FIG. 1, from the reservoir into the first tubing part 1, through the one-way valve 3 and the second tubing part 10 into the injection needle and delivered in the patients' vein.

From the above it will be clear that any contamination originating from the patient penetrates the second tubing part and could in principle reach the one-way valve, after having passed the releasable connection. The one-way valve will however inhibit any further back-flow towards that fluid dispensing unit as it only permits a flow from the fluid dispensing unit to the patient. It will be clear that the first tubing part between the one-way valve and the fluid dispensing system, functions as a kind of safety zone, and permits to additionally minimise the risk to contamination of the fluid dispensing system in case any contamination might end up in and past the one way valve. Thus a system is provided, showing doubled safety.

In particular when use is made of a tubing with a small diameter, with the disposable set of the present invention flushing may be done with a diluted contrast medium which is a mixture of physiologic fluid and contrast medium as the reduced volume of the tubing permits to reduce losses of the contrast medium. This is preferred as otherwise the initial concentration of the contrast medium may be too low to give reproducible imaging.

Disconnecting the first and second part of the connecting device permits to perform a reflux control by aspirating the dosing device and in that way permits to verify whether or not the injection needle has been inserted into the vein in a correct manner. In case the needle has been inserted into the patients' vein, a back flow of blood from the patient into the second tubing part 1 will be observed upon aspirating. In case the needle is not inserted in the vein, no back flow of blood will be observed and the needle has to be re-inserted.

The present invention also relates to a fluid dispensing system containing the above described disposable set.

The present invention further relates to a method for verifying insertion of a dosing device into a patients' vein.

This method comprises the steps of
1) inserting a dosing device, in particular a injection needle into a patients' vein,
2) temporarily loosening the connection between the first and second connector part 11, 12 to permit a back flow of blood into the second tubing part,
3) establishing the back flow,
4) re-connecting the first and second connector part 11, 12 to permit a flow from the reservoir to the dosing device.

The invention claimed is:

1. A fluid dispensing system containing a fixed, re-used part and a disposable set (5) connected to the fixed part for establishing a fluid connection between a fluid dispensing unit (17) and a dosing device which is adapted to dispense a fluid into a patient's vein, the disposable set consisting essentially of a length of a tubing (15) for establishing the fluid connection from the dispensing unit towards and into the dosing device, characterized that the tubing (15) consists essentially of a first (1) and a second (10) tubing part, wherein the first tubing part (1) comprises a first end connector (2, 11, 16, 22) to establish at a first end part (4) a connection to a third end connector (12, 13) at a second end part (9) of the second tubing part (10), and a second end connector (7) at a second end part (14) connected to the fixed part to establish a connection towards the fluid dispensing unit, wherein the second tubing part (10) comprises a fourth end connector (8) which is provided to establish at a first end part (6) of the second tubing part a connection towards the dosing device and a patient and a third end connector (12, 13) at a second end part (9) of the second tubing part (10) to establish a connection to the first tubing part (1), wherein the first tubing part (1) comprises a one-way valve (3) which is provided to permit a fluid flow from the dispensing unit (17, 18) towards the dosing device and to prevent a backward fluid flow from the dosing device towards the dispensing unit, wherein the first end part (4) of the first tubing part and the second end part (9) of the second tubing part (10) are in fluid connection with each other in a liquid tight manner by means of a releasable connection device (11, 12), which a releasable connection thereof in the released position of the releasable connection is adapted to permit a back flow from the patient into the second tubing part (10) so as to allow a back flow of blood from the patient's vein into the second tubing part and a so-called reflux blood control of blood from the vein into the dosing device and part of the tubing to permit verification of whether the dosing device has been correctly inserted into the patient's vein and so as to prevent a back flow from the patient in a direction of the releasable connection device (11, 12) in the closed position of the releasable connection so as to avoid contamination of the fixed, re-used part of the fluid dispensing system when dispensing the fluid to the patient.

2. A fluid dispensing system as claimed in claim 1, characterized in that the releasable connection device comprises a first (11) and a second connector part (12), in that the second connector part (12) is fastened to a second end part (9) of the second tubing part (10) and in that the first connector part (11) is mounted to an outlet side (2) of the one-way valve (3) along which the fluid flows from the one-way valve in a direction of the second tubing part (10).

3. A fluid dispensing system as claimed in claim 2, characterized in that the first connector part (11) is positioned on an end part of the one-way valve on a side of the one-way valve that points towards the second tubing part (10).

4. A fluid dispensing system as claimed in claim 2, characterized in that the first connector part (11) comprises a first luer lock flange which is adapted to be at least partly received within in a corresponding duct (13) of the second connector part (12) in a liquid tight manner, to establish the a fluid connection between the first and the second connector part.

5. A fluid dispensing system as claimed in claim 4, characterized in that the liquid tight connection of the first and second connector part (11, 12) is achieved by means of a bayonet coupling or a threaded connection on an outer wall of the duct (13) and an inner face of a circumferential wall (16) surrounding the first luer lock flange.

6. A fluid dispensing system as claimed in claim 1, characterized in that the releasable connection device (11, 12) is a luer connector.

7. A fluid dispensing system as claimed in claim 1, characterized in that the second tubing part (10) has a length which is longer as compared to a length of the first tubing part (1).

8. A fluid dispensing system as claimed in claim 1, characterized in that the dosing device is an injection needle.

9. A method for verifying blood back flow from a patient towards a fluid dispensing reservoir using the fluid dispensing system of claim 1, characterized in that the dosing device is inserted into the patient's vein, in that the dosing device is connected to the second tubing part (10) at the first end part (6), in that the releasable connection device (11, 12) is opened to permit the back flow from the patient's vein into the second tubing part (10), in that the releasable connection device is re-connected after the back flow of blood into the second tubing part has occurred and has been observed.

10. Use of the fluid dispensing system of claim 1 for dispensing the fluid into the vein of the patient.

11. Use of the fluid dispensing system of claim 1 for dispensing the fluid to the patient.

* * * * *